United States Patent [19]
Hartsough

[11] 3,955,586
[45] May 11, 1976

[54] BUFFER TREATED POLYURETHANE FOAM END WRAP

[75] Inventor: Lloyd Bruce Hartsough, Green Township, Hamilton County, Ohio

[73] Assignee: The Procter & Gamble Company, Cincinnati, Ohio

[22] Filed: Apr. 2, 1975

[21] Appl. No.: 562,287

[52] U.S. Cl.......................................... 132/7; 424/71
[51] Int. Cl.² ........................................... A45D 7/00
[58] Field of Search .............. 132/7, 40, 42; 424/71, 424/72

[56] References Cited
UNITED STATES PATENTS

| | | | |
|---|---|---|---|
| 2,990,832 | 7/1961 | McDonough | 132/7 |
| 3,345,993 | 10/1967 | Haefele | 132/7 |
| 3,465,759 | 9/1969 | Haefele | 132/7 |

*Primary Examiner*—G. E. McNeill
*Attorney, Agent, or Firm*—Douglas C. Mohl; Ronald L. Hemingway; Richard C. Witte

[57] ABSTRACT

A superior end wrap comprising an open-celled polyurethane foam of specified porosity and thickness which foam has been treated with a buffer solution and a permanent waving process using said buffer treated end wraps.

10 Claims, No Drawings

BUFFER TREATED POLYURETHANE FOAM END WRAP

BACKGROUND OF THE INVENTION

1. Field of the Invention

This invention relates to buffer treated polyurethane foam end wraps for use in the cold permanent waving of hair. Further, the invention relates to the process of using the end wraps in cold permanent waving.

2. Prior Art

Cold permanent waving of hair has been a popular means of waving hair for a number of years. This popularity is due to the greater convenience for this method over other methods where externally applied heat is needed to achieve the desired result. This additional convenience has permitted nonprofessional consumers to wave their hair in their own homes. In cold waving, the waving is accomplished by applying a reducing agent to the hair which causes the hair to be "softened" (the disulfide linkages present in the keratin of hair are broken). This reducing step may be done after the hair has been sectioned into individual tresses but before it has been rolled onto curlers, after the rolling has been accomplished or at both times. After sufficient time has elapsed the hair is rinsed and neutralized by chemical or air oxidation, which step reforms the disulfide linkages broken in the aforementioned reducing step.

Cold permanent waving is not without its problems however. The materials are oftentimes somewhat difficult to use with the desired result not always achieved. For example, the ends of the hair present particular problems from a handling point of view, as well as from a hair damage point of view. In the waving process, the free ends of the hair must be wound about a cylindrical body (a curler) and this presents some difficulty. To overcome this problem most commercial waving kits contain small square or rectangular pieces of paper or other material (end wraps) which are folded and placed around a hair tress in such a manner that they embrace the free end of the tress. Among the types of materials used for the end wrap are permeable polyurethane as disclosed by Haefele in U.S. Pat. No. 3,345,993, issued Oct. 10, 1967; impermeable polyurethane as disclosed by Haefele in U.S. Pat. No. 3,465,759, issued Sept. 9, 1969; and paper as disclosed by Bonilla in U.S. Pat. No. 2,991,790, issued July 11, 1961.

The end wraps which have been disclosed in the prior art are well known to be helpful in the winding process. However, they do not fully protect the ends of the hair. The desirability of protecting the ends of the hair in permanent waving stems from the fact that repeated use of conventional waving procedures is often accompanied by an overexposure of the hair ends which are susceptible to damage because of the age of the hair at the ends and the stress the ends are exposed to during the winding process. Such ends, when subjected to renewed cold waving treatments, generally exhibit undue frizziness, curling, harshness and dryness because frequent treatment is believed to unduly stress and overexpose the hair ends in renewing or repeating the waving process. There have been attempts in the past to treat the end wraps with chemical agents so that the waving solution is counteracted before reaching the hair ends (see, for example, the aforementioned Bonilla reference). Also included in such attempts was the treatment of paper end wraps with citric acid. Apparently this approach did not yield satisfactory results due to an insufficient benefit being obtained and stability problems associated with cellulose (paper) in an acid environment.

Accordingly, it is an object of this invention to provide effective buffer treated end wraps which are useful in the keratin modification process.

It is a further object to provide an improved method for permanently waving hair.

Other objects and advantageous features will be apparent from the following detailed description.

DETAILED DESCRIPTION OF INVENTION

The present invention resides in the discovery of an improved end wrap comprising a flexible wafer of porous polyurethane foam having a thickness of from about 1/64-inch to about 1/16-inch and a solid, water-soluble buffer having a pH of from about 3 to about 6, wherein said buffer is contained in said wafer.

The polyurethane foam end wraps used as the starting material for this invention are those of U.S. Pat. No. 3,345,993, Oct. 10, 1967, to Haefele incorporated herein by reference. These end wraps are preferably either square or rectangular in shape and have dimensions within the range from 1⅜ × 1⅜ inches to 4 × 4 inches. An especially preferred size and configuration is a rectangular wafer having the dimensions 3 × 2 inches.

The thickness of the untreated foam end wraps can vary within the range of 1/64 to 1/16 inch. As the length and width are increased, a thinner end wrap should be used. Foam end wraps which are thinner than about 1/64 inch are difficult to process and do not have sufficient tear strength for the intended use. End wraps having thicknesses greater than about 1/16 inch yield too large a curl. The preferred thickness for the purpose of this invention is 1/32 inch.

The degree of porosity of the end wrap must be sufficient to permit substantially unimpeded flow of the waving and neutralizing solutions. An average pore incidence from about 30 to about 120 pores per linear inch is necessary for adequate flow. More numerous pores are preferable in the case of thinner end wraps. The preferred end wraps have an average of 80 pores per linear inch.

Polyurethane foams are divided into two major categories based on the polyols used in their preparation — either polyether polyols or polyester polyols. The polyester foams are especially preferred for this purpose of this invention, since they have better solvent resistance and better color stability in the presence of ultraviolet light. These foams can be prepared by a variety of methods which are well known in the art. Essentially, such foams are made by the condensation of organic isocyanates, such as tolylene diisocyanate, with polyols such as polyethylene ether glycol, in the presence of a catalyst and a blowing agent. Basic processes and apparatus for preparing such foams are disclosed, for example, in U.S. Pat. No. 2,764,565, issued Sept. 25, 1956, incorporated herein by reference.

The buffer with which the foam end wraps of this invention are treated can be any buffer system which is a solid and has a pH of from about 3 to about 6 (said pH being the pH of a 25°C. aqueous solution of the buffer system at a concentration of from about 0.2% up to the solubility limit of said buffer system). Preferably the buffer should have a pH of from about 4 to about 6, should be soluble in water to an extent of at least about 7% and should have a melting point greater than about 95°C. The pH should not be lower than 3 or higher than 6 to ensure that the polymer is not degraded and yet that the sufficient neutralization potential is present to act on the waving lotion. Examples of suitable buffer systems are dibasic sodium phosphate/monobasic sodium phosphate, monobasic sodium phosphate, sodium citrate/citric acid, dimethylglutaric acid/sodium hydroxide, succinic acid/sodium hydroxide, potassium acid phthalate/sodium hydroxide, sodium acid maleate/sodium hydroxide and potassium monobasic phosphate/sodium hydroxide. In those instances where the buffers consist of more than one component the components are used in the ratios necessary to produce the desired pH. A preferred group of buffers is dibasic sodium phosphate/monobasic sodium phosphate, monobasic sodium phosphate, and potassium acid phthalate/sodium hydroxide.

It has been found that the amount of buffer present in the foam end wraps of this invention can vary depending on the thickness and outside surface area of the wrap, but a minimum level of 5 milligrams of buffer/cubic inch of foam is thought to be required to ensure that protection is obtained. It is preferred, however, that the amount of buffer present be from about 9.0 milligrams to about 300 milligrams per cubic inch of foam. This range allows the ends of the hair to be adequately protected while still ensuring that they receive some wave.

The foam end wrap material may be conveniently treated by use of a water solution of the buffer. The material may be passed through the water solution, or the solution may be brushed or sprayed onto the material. The treated material is then dried by means of a drum dryer or oven, air exposure or by other suitable means to remove the moisture present. The concentration of buffer in the water solution depends on the buffer used, the method of application employed and the buffer concentration desired in the treated foam end wraps. The concentration of buffer typically would be in the range of about 0.2% to about 60%. (Of course, the upper limit is subject to the solubility of the buffer system used.)

To decrease the likelihood of the end wraps picking up static charge, the foam may be treated with an antistatic material such as a mineral oil mixture.

A preferred embodiment of this invention relates to the process of cold permanent waving. Use of this invention's buffer treated foam end wraps in the same manner as conventional end wraps in cold permanent waving reduces the strength of the wave given to the ends of the hair. This is believed to be due to the lowering of the pH of the reducing solution when it comes into contact with the treated foam end wrap which is around the ends of the hair. This results in a softer looking wave, with greater fullness, but with the same strength of curl as current products give except at the hair tips.

More specifically, in regard to the aspect of cold permanent waving processes, this invention comprises the steps of forming the hair into tresses, wrapping around the end of each tress a treated foam end wrap of the type disclosed herein, winding each tress about a cylindrical body, i.e., a curler, saturating each tress with a keratin-reducing composition and thereafter neutralizing the action on the hair of said keratin-reducing composition. Alternatively, the keratin-reducing composition is applied to the hair both before and after the hair is rolled upon curlers.

The keratin-reducing compositions which may be used in the permanent wave processes of this invention contain a water-soluble nonvolatile mercaptan such as mercapto-alkanoic acids, mercapto-acetic acid, mercapto-propionic acid, mercapto-butyric acid and water-soluble salts thereof. Examples of other suitable mercaptans are thioglycolic acid, sodium thioglycolate, potassium thioglycolate, monoethanolamine thioglycolate, β-mercapto isobutyric acid, thiohydracrylic acid, β-mercapto-n-butyric acid, mercapto-caproic acid, thioglycerol and thiolactic acid. These compositions have a pH of 7.0 to 9.5 which can be provided with alkaline agents such as ammonia, monoethanolamine, diisopropylamine, sodium hydroxide, potassium hydroxide and the like.

In addition to the mercaptans, it is often desirable, but not essential, to include in the keratin-reducing composition a water-soluble disulfide of the mercaptan used such as dithiodiglycolic acid, dithiodilactic acid, the disulfides of β-mercaptobutyric acid, β-mercaptoisobutyric acid, dithiodihydracrylic acid or a water-soluble salt of these acids to protect against excessive reduction and damage to the hair in accordance with the disclosures in U.S. Pat. No. 2,719,814, Oct. 4, 1955, to Haefele and U.S. Pat. No. 2,719,815, Oct. 4, 1955, to Sanders.

The permanent waving processes of this invention can also be used to advantage in conjunction with pressurized hair waving compositions which are applied to the hair as a fast-breaking foam. Examples of such compositions are disclosed by Banker et al. in U.S. Pat. No. 3,099,603, July 30, 1963, and Sheperd et al. in U.S. Pat. No. 3,103,468, Sept. 10, 1963.

The action on the hair of the keratin-reducing compositions can be neutralized by chemical compounds such as bromates, perborates, hydrogen peroxide or the action of air alone.

Certain particular embodiments of the invention are illustrated in the following examples but the invention is not intended to be limited thereto. All percentages used herein previously and subsequently are by weight unless otherwise indicated.

EXAMPLE I

One hundred parts by volume of a polyester of the following composition:

| | Moles |
|---|---|
| Adipic acid | 16 |
| Diethylene glycol | 16 |
| Trimethyol propane | 1 | are reacted with 47 parts by volume of tolylene diisocyanate in the presence of 10 parts by volume of an activator mixture of the following composition:

| | Parts by Volume |
|---|---|
| Adipic acid ester of N-diethylaminoethanol | 3 |
| Ammonium oleate | 1 |
| Sulfonated castor oil | 1.5 |
| Water | 1.5 |
| Paraffin oil | 0.5 |

The polyester is mixed with water and the other activator components and then the tolylene diisocyanate is added. The mixture is dried to remove the moisture present. The product is a slab of flexible foam of 2.2 pounds per cubic foot density, having an average of 60 cells per linear inch. The slab is then cut into 3 × 2 inches wafers or larger sheets having a thickness of 1/32 inch.

The reactants and conditions as identified above can be varied in accordance with the teachings of U.S. Pat. No. 2,764,565 to yield foams having an average of 40, 80 and 120 pores per linear inch and thickness of from about 1/16 inch to about 1/64 inch.

EXAMPLE II

Foam end wraps measuring 3 × 2 × 1/32 inches made according to Example I were dipped into a 2% aqueous solution of $Na_2HPO_4/NaH_2PO_4 \cdot H_2O$ buffer having a pH of 5.79. The amount of solution retained by each foam end wrap was 1.0g after being drained (corresponding to about 107 milligrams of buffer/cubic inch of foam.) The wraps were then allowed to air dry for a period of about 16 hours at room temperature (~75°F.).

EXAMPLE III

A sheet of polyurethane foam measuring 3 × 16 × 1/32 inches made according to Example I was dipped into a 12.31% aqueous solution of $NaH_2PO_4 \cdot H_2O$ having a pH of 4.13. The sheet, after being wrung out, retained 1.30 grams (corresponding to about 107 milligrams of buffer/cubic inch of foam) of the solution. The sheet was then let air dry for a period of about 4 hours at room temperature (~75°F.). The sheet was subsequently sprayed with a mineral oil antistat agent. As a final step, end wraps measuring 3 × 2 × 1/32 inches were cut from the sheet.

EXAMPLE IV

The acid treated foam end wraps as prepared in accordance with Example II are employed in a permanent waving process using the following keratin-reducing composition

| Component | Weight % |
|---|---|
| Monoethanolamine thioglycolate | 11.41 |
| Hydrogen peroxide | 0.34 |
| Monoethanolamine | 2.30 |
| Mineral oil | 1.555 |
| Oleic acid | 0.337 |
| Potassium hydroxide | 0.088 |
| Ethylene glycol | 0.199 |
| Perfume | 0.50 |
| Polyoxyethylene (23) lauryl ether | 1.043 |
| Color | 0.10 |
| Distilled water | 82.128 |
| | 100.000 |

The hair is washed and separated into tresses. The acid treated end wrap is folded over the wet hair tress so that it covers all of the free ends. Each wrapped tress is then wound upon a curler and secured. The keratin-reducing composition is applied to the wound tresses and after waiting 15 minutes, rinsed with water and blotted. The head is then covered with a towel and after an additional 30 minutes the hair is neutralized with a 3% hydrogen peroxide solution. The hair is removed from the curlers, again rinsed with water, set in a normal fashion and dried.

The ends of the hair are protected from the total effect of the keratin-reducing composition by the buffer treated end wraps.

What is claimed is:

1. An end wrap for use in the permanent waving process which comprises a permeable flexible wafer of open-celled polyurethane foam having a thickness of from about 1/16 inch to about 1/64 inch, an average pore incidence within the range of from about 30 to 120 pores per linear inch and, contained in said end wrap at a level of at least 5 milligrams of buffer per cubic inch of foam, a solid, water-soluble buffer system having a pH of from about 3 to about 6.

2. An end wrap according to claim 1 wherein the wafer of polyurethane foam has a thickness of 1/32 inch.

3. An end wrap according to claim 1 wherein the wafer of polyurethane foam has an average pore incidence of 80 pores per linear inch.

4. An end wrap according to claim 1 wherein the polyurethane foam is polyester urethane.

5. An end wrap according to claim 1 wherein the solid, water-soluble buffer system is selected from the group consisting of dibasic sodium phosphate/monobasic sodium phosphate, monobasic sodium phosphate, and potassium acid phthalate/sodium hydroxide.

6. An end wrap according to claim 5 wherein the solid, water-soluble buffer system contained in said end wrap is present at a level of from about 9 to about 300 milligrams/cubic inch of foam.

7. The process of imparting a permanent wave to hair which comprises the steps of forming the hair into tresses, wrapping about the end of each tress a permeable, flexible wafer of polyurethane foam having a thickness of from about 1/16 inch to about 1/64 inch and contained in said wafer at a level of at least 5 milligrams of buffer per cubic inch of foam, a solid, water-soluble buffer system having a pH of from about 3 to about 6, winding each tress on a cylindrical body, saturating each wound tress with a keratin-reducing composition and thereafter neutralizing the action of the hair of said keratin-reducing composition.

8. A process according to claim 7 wherein the wafer of polyurethane foam has a thickness of 1/32 inch and an average pore incidence of 80 pores per linear inch and the polyurethane foam is polyester urethane.

9. A process according to claim 7 wherein the solid, water-soluble buffer system having a pH of from about 3 to about 6 is selected from the group consisting of dibasic sodium phosphate/monobasic sodium phosphate, monobasic sodium phosphate, and potassium acid phthalate/sodium hydroxide.

10. A process according to claim 9 wherein the solid, water-soluble buffer system contained in said wafer is present at a level of from about 9 to about 300 milligrams/cubic inch of foam.

* * * * *